United States Patent [19]

Winckler et al.

[11] Patent Number: 5,092,175
[45] Date of Patent: Mar. 3, 1992

[54] APPARATUS FOR TESTING HARDNESS UNDER LOAD

[75] Inventors: Immo Winckler; Jürgen Kising, both of Cologne; Andreas Wiese, Bonn, all of Fed. Rep. of Germany

[73] Assignee: Krautkramer GmbH & Co., Hurth, Fed. Rep. of Germany

[21] Appl. No.: 455,412

[22] PCT Filed: Jun. 9, 1988

[86] PCT No.: PCT/DE88/00343
§ 371 Date: Dec. 21, 1989
§ 102(e) Date: Dec. 21, 1989

[87] PCT Pub. No.: WO88/10416
PCT Pub. Date: Dec. 29, 1988

[30] Foreign Application Priority Data

Jun. 23, 1987 [DE] Fed. Rep. of Germany ....... 3720625

[51] Int. Cl.[5] ............................................. G01N 29/00
[52] U.S. Cl. ..................................................... 73/573
[58] Field of Search ............... 73/573, 579, 645, 78, 73/763, 774, 778

[56] References Cited

U.S. PATENT DOCUMENTS

| | | | |
|---|---|---|---|
| 3,572,097 | 3/1971 | Kleesattel | 73/579 |
| 3,955,404 | 5/1976 | Bickel et al. | 73/573 |
| 3,958,450 | 5/1976 | Kleesattel | 73/579 |
| 4,646,571 | 3/1987 | Kising et al. | 73/573 |

Primary Examiner—Hezron E. Williams
Assistant Examiner—Louis M. Arana
Attorney, Agent, or Firm—K. S. Cornaby

[57] ABSTRACT

An apparatus for testing hardness under load has a measuring sensor in the form of a manual apparatus in which a mobile rod-shaped resonator can be slidingly inserted. The free end of the resonator, situated outside the housing, has a measuring tip. The resonator is held against the housing of the measuring sensor by a spring and is linked to ultrasonic converters connected to an electronic generator and to a receiving circuit which records changes in the duration or frequency of the vibrations of the generator. A basic apparatus comprises a display unit and is connected by a connecting line to the measuring sensor. A memory for storing individual parameters of the rod-shaped resonator and the electronic generator is arranged in the housing of the measuring sensor. The basic apparatus is detachably connected by insertion to the measuring sensor.

11 Claims, 2 Drawing Sheets

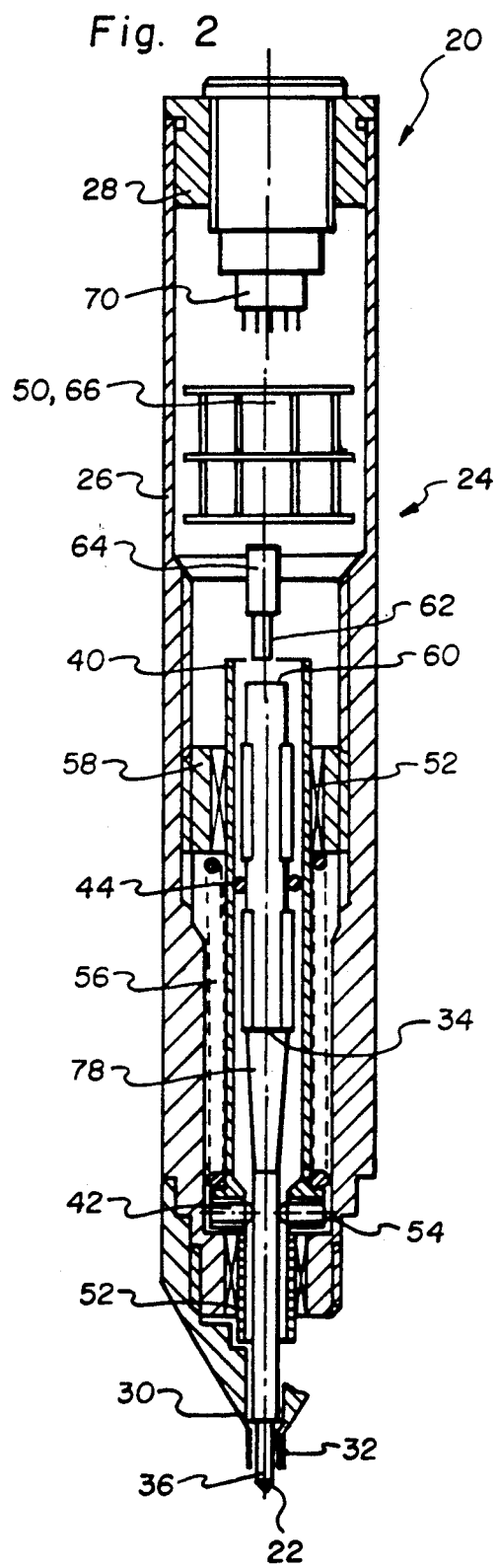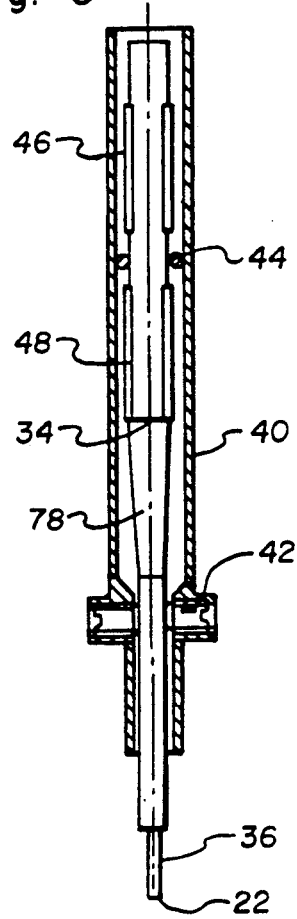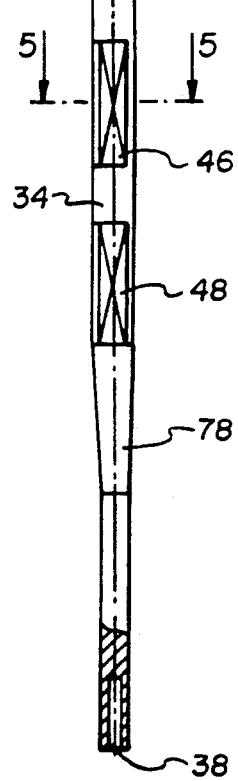
Fig. 2
Fig. 3
Fig. 4
Fig. 5

APPARATUS FOR TESTING HARDNESS UNDER LOAD

BACKGROUND OF THE INVENTION

The invention pertains to a device for testing hardness under load. It has at least one measuring sensor in the form of a manual apparatus. This manual apparatus has a pencil-like housing in which a mobile rod-shaped resonator can be slidingly inserted. The resonator has (a) on its free end, which is situated outside the housing, a measuring tip;

(b) and the resonator is held against the housing of the measuring sensor by a spring.

(c) The resonator is linked to ultrasonic converters that are connected to an electronic generator or to a receiving circuit that records changes in the duration of frequency of the vibrations of the generator.

The device incorporates also a basic apparatus that comprises a display unit and is connected by a connecting line to the measuring sensor.

In the resonance process for testing hardness which is familiar from U.S. Pat. No. 3,572,097 frequently designated the UCI-(Ultrasonic Contact Impedance)—process, a rod-shaped resonator is activated longitudinally with the help of piezo-electric ultrasonic converters to produce vibrations. In this device a rod with the dimension ratio $1 \times \frac{1}{4}$ is employed, thereby ensuring that only the first overtone can be formed. The rod is fitted on its lower, free end with a penetrating device that is manufactured of diamond. When this system is coupled elastically to a mass or body the resonating frequency of the resonator is modified to higher values because an additional repulsion (resetting) force acts on the resonating system. The value of this repulsion force and with it the modification to which attention has been drawn are dependent on the surface of contact between the penetrating body and the body to be tested and the elastic property of this surface.

In each instance the variation in frequency is a function of the surface of contact, the elasticity modulations of the diamond or, respectively, of the body to be tested, the Poisson's ratio of the diamond or, respectively, of the body to be tested and the resonating frequency of the resonator. If the elasticity modulations and Poisson's ratio are not known the testing device of the familiar kind can be calibrated by means of a comparison (calibration) plate of the kind that is already well known. Thus it is possible to carry out measurements on bodies whose elastic constants vary just a small amount from those of the calibration plate, it being necessary in instances where the resonance frequency is known to measure only the frequency variation. In practice it has been found that non-alloyed steels and steels with a low alloy have to a very large extent overlapping elasticity modulations or, respectively, Poisson's ratios; the calibrations process is therefore particularly suited for steels of this kind. The apparatus for testing hardness under load of the kind to which attention was drawn above is familiar from the journal article "VDI-Report Number 583/1986, pp. 371–391". In this device, which is designed predominantly for testing small loads, all the electronic parts but especially the electronic generator, which is designed to stimulate the resonator, and the electronic receiving circuit are sited in the analyzer. Just one sensor is attached to each analyzer, and sensor and analyzer are attuned to each other. Thus it is possible to exchange one sensor for another only if the analyzer is calibrated anew each time. This is a disadvantage. In general, when measuring under various testing pressures several devices for measuring hardness are employed because too much time is required to calibrate anew the sensors. On the other hand, attempts to manufacture the sensors so accurately that one can be exchanged for another have shown that variations which always result during manufacture can be avoided only at unusually huge expense, for which reason it is not possible to achieve in this way an economic solution to this problem.

In the apparatus for testing hardness of the kind mentioned above the spring that is sited between the rod-shaped resonator and the housing for the measuring senso is designed as a tension roll spring. Such springs are, on the one hand, bulky, and on the other hand, expensive. The tension roll spring determines essentially the dimensions of the measuring sensor.

The German Patent Document 33 29 690 describes a process and a device for simplifying the testing procedure in accord with the Contact Impedance Method. In this process the vibrations of the freely resonating rod-shaped resonator are measured over an initial or first period of time, and then, in a second time period that is of the same duration, the vibrations of the resonator, which is now connected to a test-piece, is measured. During the second time period the vibrations of the resonator that are coupled to the test piece are counted only until zero value is achieved in the subtraction of this value and the value that was ascertained during the vibrations in the first time period; during the time remaining in the second time period the vibrations are counted over strictly delimited period. In one version of the device the length of the first time period is set at 355 ms. The German Patent Document 35 04 535 describes for determining the hardness of solid bodies a process that essentially is completed with a device such as is outlined in the above-mentioned VDI-report. In this process, however, no differences in frequency are measured; rather, the process determines the amplitude of the rod-shaped resonator when it is mechanically coupled with the body to be tested, and from the square of the amplitude values the hardness of the subject body can be calculated.

SUMMARY OF THE INVENTION

Proceeding from the apparatus for testing hardness of the kind that is mentioned in the introductory remarks it is the purpose of the invention to avoid the disadvantages of this kind of apparatus for testing hardness and, subject to this, to achieve such reduction in size of the measuring sensor that it will be possible to connect a number of measuring sensors one after the other to one and the same analyzer and use (various) measuring devices with various analyzer.

Proceeding from the apparatus for testing hardness of the kind that is mentioned in the introductory remarks this purpose is achieved by means of a device and its special features. These include: a memory for storing individual parameters of the rod-shaped resonator, the electronic generator and a switch for triggering the (receiver side) measurement procedure for the duration of the vibrations of the resonator. These are arranged in the housing of the measuring sensor, the resonator being fitted with a releasing device that reacts to the position of the adjustable resonator and the spring being a coil (helical) spring.

In this apparatus for testing hardness the data that are required for calibration are contained in the memory which, preferably, enables the information to be stored permanently (for example, $E^2$—prom). In this way each individual sensor has stored in itself, which is to say in its memory, the features which are characteristic for it, thereby rendering unnecessary the complicated task of calibrating anew in order to adapt the individual parameters of the sensors to the reduction instrument. It is thus possible to keep in reserve for use with one basic apparatus several sensors which have been calibrated for various materials or readied for various testing pressures. Because the stimulating sender too is housed in the measuring sensor itself its influence on the calibration will be minimal, and in this way the exchangeability of individual measuring sensors is considerably improved. In principle, however, it is possible—in an inferior version—to continue to site the electronic generator in the analyzer. This does not cause difficulties if one works with only one analyzer. But if one wishes to employ severa analyzers it is then especially advantageous for problem-free exchange if the electronic generator that is especially calibrated for the particular rod-shaped resonator is present.

When general reference is made to the individual parameters of the rod-shaped resonator then it must be understood that we are not referring simply to the parameters of the naked resonator rod but also to the parameters of the ultrasonic converters which are attached to it, the properties of the particular connection between these ultrasonic converters and the actual rod, the concrete proportions of the support of the resonating rod in the housing etc.

A micro-calculator is incorporated in the basic. By means of the items of information that are contained in the individual memory of the measuring sensors this micro-calculator, by making reference to constant parameters and the measured frequency variation or, respectively, the duration of the period, calculates the degree of hardness This is then read off the dial (scale) by the user. The individual measuring sensors are calibrated for various testing forces, typical testing forces being 2, 5, 10, 20 and 50N.

If a coil spring is employed in place of a tension roll spring the measuring sensor of the apparatus for testing hardness that is constructed in accord with details of this invention can be made smaller than it is in the devices already available. In particular, it can have a smaller diameter At the same time, the coil spring ensures higher testing forces. Although in devices that are constructed using a tension roll spring the testing force must by reason of the characteristics of the spring remain below 10N, in devices that employ a coil spring the value chosen can be higher, for example, 50N. In addition, two separate cylindrical springs can be incorporated one behind the other, and these then constitute the spring. The device can, for example, incorporate a soft spring which ensures that during manual operation the contact force on the measuring sensor is not too high, thereby preventing damage to the diamond. Once the first, relatively soft spring is compressed then the second, more resilient spring, which records the testing force, comes into play.

The use of a coil spring is nevertheless disadvantageous in that the spring tension is dependent on the travel of the spring, whereas in a tension roll spring the spring tension is largely independent of the travel. Now in order to ensure that the operator is working always with a constant testing force a switch for triggering the receiver-side measuring process is incorporated in the housing of the measuring sensor. This switch has a triggering component which reacts to the position of the moveable, rod-shaped resonator. During measurement the measuring sensor is first placed gently on the surface of the body to be tested, and then the application force is gradually increased. The spring is thereby compressed and the resonator is moved into the housing of the measuring sensor. When it reaches a position that corresponds to the chosen testing strength the triggering component is activated, thereby activating the switching procedure. This ensures that the operator is always working with a known, given testing force. Adjusting the position of the triggering component will vary the testing strength of the sensor.

It has proven to be particularly advantageous—especially in conjunction with the switch configuration that has just been outlined—to set the receiving circuit for a measurement over a short period of time, for example, 20 ms. For measurements of this kind, which succeed one another in a relatively short period of time, it is more advantageous to measure the duration of the vibration and not the frequency. By reason of the relatively short period of time that is needed to determine the duration of the vibration the result is largely independent of the constancy over time of the testing force during the actual period of measurement. Thus the device that is constructed in accord with this invention is especially suited to manual use. In particular, it can be grasped manually and pressed on to the body to be tested, and during testing the user can be alerted—via the display which eventuates, for example, or via an acoustic signal—to the fact that he/she has achieved the given testing strength and that the measurement can be completed. But the measuring sensor can also be transported in a tripod and pressed by the user against the body to be tested. The measuring sensor which is constructed in accord with the details of this invention is also suitable for machine application, for example, in robots.

Finally, in a further development it has also proven advantageous to construct the rod-shaped resonator in such a way that it tapers from the end area which is sited inside the housing of the measuring sensor to the end area that is free. It is advantageous if this tapering is achieved in stages. The thinner the resonator is constructed the greater is the frequency change when the device is applied to a body that is to be tested. On the other hand, it is difficult in a relatively thin, rod-shaped resonator to incorporate ultrasonic converters that are large enough, which is to say ultrasonic converters that do not have too small a surface area. In this connection the invention suggests that the rod-shaped resonator be constructed in such a way that the free end of the area which protrudes out of the housing has a smaller cross-section than the area at the other end on which the ultrasonic converters are mounted. The cross section ratio is preferably greater than the order of 1 to 2. If constructed in this way the rod will, on the one hand, be thick enough at its inner end to enable ultrasonic converters that are large enough to be attached. The larger the converters are the greater is the sensitivity of the resonator, as the resonance amplitude increases with the diameter. On the other hand, the relatively small diameter at the other end, for example 1 mm, ensures that possible applications of the testing device that is constructed in accordance with this invention are considerably increased. In addition, as mentioned, the variation in frequency is greater. This results in greater accuracy, and this is especially advantageous when testing is to be completed in a short period of time. By reason of the very small dimensions in the testing area, which is to say in the vicinity of the diamond, it is possible to take measurements on the sides of cog(wheel)s and on places which were not accessible with the testing devices that are already available. For example, it is possible to test the hardness of welded seams, the inner surfaces of pipes of relatively small diameter and segments of concave surfaces.

Finally, it is advantageous to site the diamond that serves as the testing agent in a restraint (holder) which can be attached to the free end of the resonator. In the event that the diamond should be damaged it can be exchanged without great difficulty perhaps even by the user.

Further advantages and characteristics of the invention will be evident from the following description of one possible embodiment of the device, it being understood that the description does not limit in any way other embodiments. This version is described with reference to the drawings.

BRIEF DESCRIPTION OF THE DRAWING

In these:

FIG. 2 a longitudinal section through a measuring sensor of a device for testing hardness that is constructed in accord with the principles of the invention;

FIG. 3 detail of a section of FIG. 2, specifically, the complete resonating rod;

FIG. 4 a side view—partly shown as a cross section—of a rod shaped resonator; and FIG. 5 a cross section along the V—V line in FIG. 4.

DETAILED DESCRIPTION OF THE DRAWING

Figure 1:
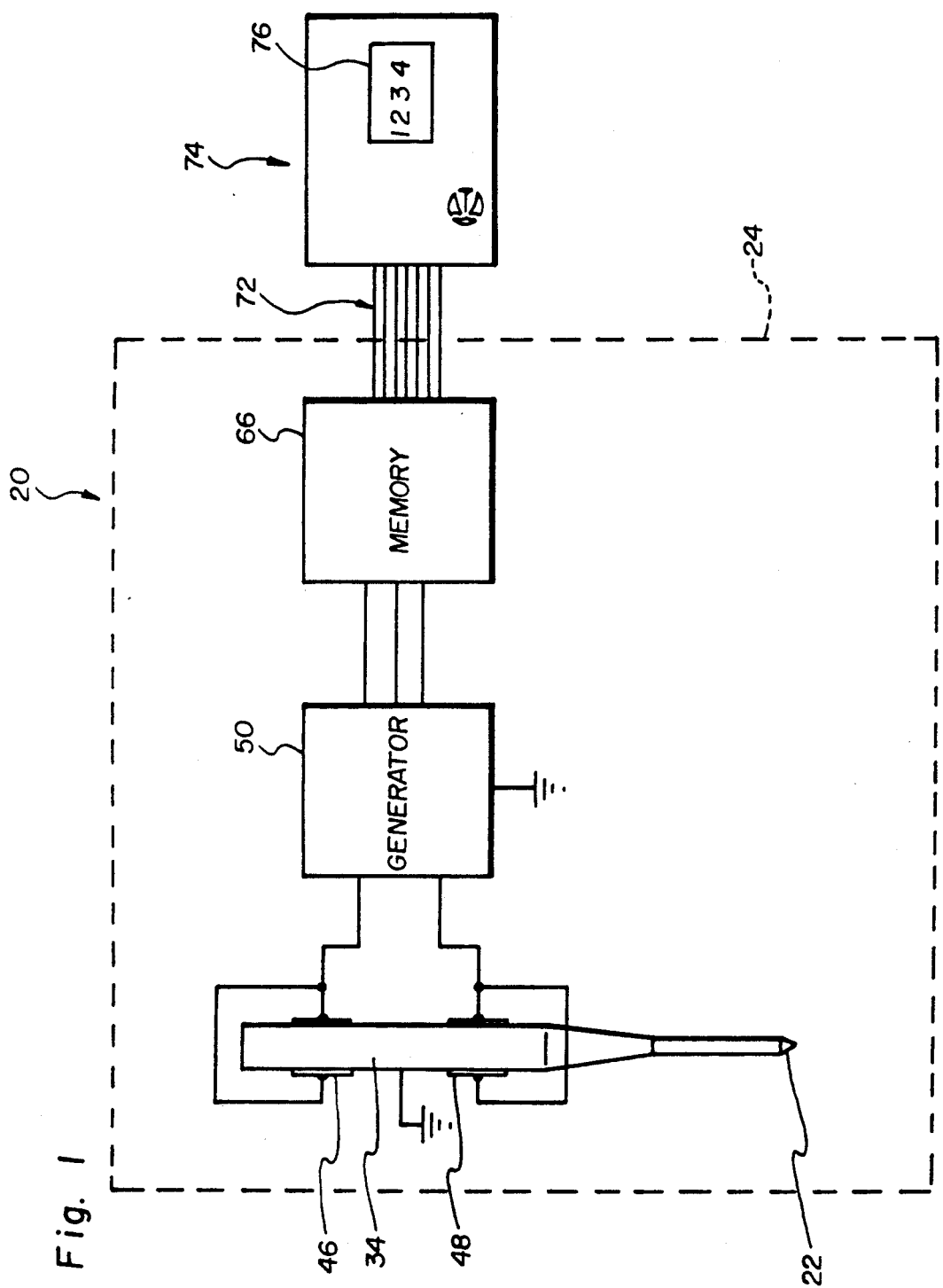
FIG. 1 a representation of the principles of the testing device in accord with the idea of this invention. It has a measuring sensor, the housing of which is indicated by the shaded rectangle, and a basic device that is equipped with a numerical display. (The connection wire is shown.)

As shown in FIGS. 1-5, the apparatus for testing hardness under load has at least one measuring sensor (20) that has a pencil-like housing (24) which is essentially cylindrical and which tapers to its testing point (22). In FIG. 1 the housing is indicated by the shaded rectangle, and details of the housing itself are evident from FIG. 2. According to this figure it consists essentially of a cylindrical section (26) which externally is cylindrical but which is stepped on its inner surface. The upper opening of this cylindrical body has a cover (28), and at its lower end it may be extended, in the event that it is necessary to work with extension sections (32), by a sleeve (30) which is in part conical in shape and which can be screwed onto the thread of the cylindrical body (26).

A mobile rod-shaped resonator is sited inside the housing (24). This rod-shaped resonator normally projects just a little—for example 15% of its total length—beyond the lower end of the cylindrical body (26) When the sleeve (30) is attached just the diamond, which constitutes the measuring tip (22), and its own rod-shaped holder (36) are visible. This holder has a diameter of 1 mm and is, for example, 8 mm long. It is mounted in a downward-facing slit (38) of the resonator (34) in such a way that holder (36) and measuring tip (22) can be exchanged.

The resonator (34) is surrounded in the cylindrical body (26) by the guiding tube (40). In its lower region it displays a thread, and there the resonator (34) is mounted by means of fixing screws (42). An 0-ring (44) is mounted at the appropriate distance from the inner end of the resonator (34) between the guiding tube (40) and the resonator (34). On both sides of this 0-ring (44) pairs of ultrasonic converters are attached to it in the appropriate recesses in the resonator (34). (See FIG. 5.) The ultrasonic converters (46) that are mounted between the 0-ring (44) and the inner, free end are connected electrically with a generator (50) and serve to stimulate the resonator (34). The ultrasonic converters (48) that are mounted more to the geometric center of the resonator (34) and on the other side of the O-ring (44) are connected electrically to a receiving circuit that is not shown in the drawings. This is constructed in such a way that the periodic duration of the mechanical vibrations of the resonator (34) is registered and transmitted to a micro-calculator. (It too is not shown.)

The guiding tube (40) is enclosed by two cylindrical slide bearings (52). The first of these is sited in the lower area of the cylindrical body (26). Above this slide bearing (52) the inner diameter of the cylindrical body (26) increases in order to create space for the fixing screws (42). The pertinent section of the guiding tube (40) serves at the same time as its lower point of contact and hence as a limit to the travel of the guiding tube (40) (including the resonator 34). Contact is effected at an inner step (54). On the opposite side to the step (54) a cylindrical spring (56) is supported on inserts for the fixing screws (42). This spring has an inner diameter that is but minimally larger than the external diameter of the guiding tube (40), and it is supported on a sleeve-shaped fixing screw (58) which is connected via its inner sleeve to the second slide bearing (52). Its external cover has an external thread which is aligned with an inner thread on the inner wall of the cylindrical body (26) and which can be screwed in from above, which is to say from the side on which the cover (28) is mounted.

The total length of the resonator (34) is approximately 55 mm. Its inner end (60) is sited approximately halfway along the cylindrical body (26). The typical displacement of the resonator (34) with its guiding tube (40) is approximatelty 1.5 mm. FIG. 2 shows the resonator (34) in the rest position In this position a triggering device (62) of a centrally arranged switch (64) is not in contact with the end (60). In the event that the resonator (34) together with its guiding tube (40) is pushed into the housing (24) because the measuring tip (22) is placed on a body to be tested—this body is not shown in the drawings—then the end (60) makes mechanical contact with the triggering device (62). This activates the switch (64), and the measurement is effected.

The switch (64) can also be configured differently from the version that is shown in the drawings. It can, for example, have the form of a proximity switch, a software switch, a light barrier, a contact switch or the like. It is advantageous if the switch (64) or, respectively, its triggering device (62), does not limit the path of the resonator (34) upwards.

The cylindrical body (26) of the housing (24) has its thinnest wall between the switch (64) and the cover (28). The electronic component of the sensor, which consists of a store (66) and a generator (50), is mounted in this region. These are shown in FIG. 1 but are not detailed in FIG. 2. The electronic component of the sensor is connected via contacts to a plug connection (70). This plug connection is encompassed by the cover (28), and it is accessible from the upper face of the housing (24). A connection (72) that is detachable is attached by means of a second plug connection—not shown in the drawings—to this plug-connection. (See FIG. 1.) This links the measuring sensor (20) with a basic device (74) in which both a display unit (76), which in this version records numerically, and a micro-calculator are housed. (The micro-calculator is not shown) The hardness that has just been tested is immediately displayed by means of the display unit (76).

The resonator (34) is, proceeding from the end (60), cylindrical for approximately 50% of its length. In the version described it has a diameter of 3 mm. This cylindrical shape changes at the bluntly spherical region (78) to a second cylindrical section which comprises 32% of the total length and in which the slit (38) is sited.

The data that are stored in the store (66) have regard to the individual characteristics of the whole vibrating rod arrangement. They are calculated semi-automatically by means of three-point adjustment and standardized testing plates. It is possible to use for this adjustment the micro-calculator that is incorporated in the basic apparatus (74), or another calculator may be employed.

We claim:

1. An apparatus for testing hardness under load comprising (a) at least one measuring sensor in the form of a manual apparatus having a pencil-like housing in which a mobile rod-shaped resonator is slidingly inserted which resonator has at its free end, which protrudes beyond the housing, a measuring tip; and is held against the housing by a spring; and is fitted with ultrasonic transducers that are connected to at least one of an electronic generator and a receiving circuit which records changes in the duration or, respectively, the frequency of the vibrations of the resonator; and (b) an analyzer that is fitted with a display element; and (c) a memory sited in the housing of the measuring sensor for storing individual parameters of the rod-shaped resonator and the electronic generator, the analyzer being connected by a detachable connection with one of the measuring sensors.

2. An apparatus for testing hardness as set forth in claim 1, wherein for any one given testing strength various measuring sensors are available.

3. An apparatus as set forth in claim 1, wherein a switch for triggering the receiver side measuring process for the duration of vibration of the resonator is sited in the housing of the measuring sensor which switch has a triggering element that reacts to the position of the moveable resonator.

4. An apparatus for testing hardness as set forth in claim 1, wherein the receiver electronic is designed for measuring over a short time span the duration of frequency of vibration of the resonator.

5. An apparatus for testing hardness as set forth in claim 1, wherein the spring is a coil spring.

6. An apparatus for testing hardness as set forth in claim 1, wherein several springs that have varying spring tensions are incorporated, being arranged one behind the other.

7. An apparatus for testing harndess as set forth in claim 1, wherein the rod-shaped resonator reveals on its free end, which end is connected to the measuring tip, a cross-section that is round and smaller than the cross-section at its other end, the cross-section ratio being greater than 1 to 2.

8. An apparatus for testing hardness as set forth in claim 7, wherein the resonator is cylindrical over approximately half of its total length, which cylinrdical section has a greater diameter, and at this point changing via a blunty spherical section to a cylindrical section with a smaller diameter, this second cylindrical section comprising approximately 32% of the total length of the resonator.

9. An apparatus as set forth in claim 7, wherein the resonator has a slit on its end area that borders on the measuring tip.

10. An apparatus as set forth in claim 7, wherein the measuring tip is connected with a hodler which is connected via a detachable connection to the free end of the resonator.

11. An apparatus for testing hardness as set forth in claim 7, wherein the resonator is surrounded over most of its length by a guiding tube, which guiding tube reveals inserts for fixing screws which on the one side function together with a step and on the other provide support for the screw.

* * * * *